US011617662B2

United States Patent
Tsukayama et al.

(10) Patent No.: US 11,617,662 B2
(45) Date of Patent: Apr. 4, 2023

(54) ORTHOPAEDIC SURGICAL INSTRUMENT SYSTEM AND METHOD FOR DETACHING TRIAL CONSTRUCT ASSEMBLIES

(71) Applicant: DEPUY IRELAND UNLIMITED COMPANY, Ringaskiddy (IE)

(72) Inventors: Craig S. Tsukayama, Fort Wayne, IN (US); Phillip G. Withee, Fall River, MA (US); Jeremiah M. Lewis, Leesburg, IN (US); Charles L. Penninger, Warsaw, IN (US); Francisco A. Amaral, Acushnet, MA (US); Tyler S. Hathaway, Auburn, IN (US); Daniel E. Lashure, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 326 days.

(21) Appl. No.: 17/094,258

(22) Filed: Nov. 10, 2020

(65) Prior Publication Data
US 2021/0052398 A1 Feb. 25, 2021

Related U.S. Application Data

(62) Division of application No. 15/704,324, filed on Sep. 14, 2017, now Pat. No. 10,828,173.

(51) Int. Cl.
*A61F 2/46* (2006.01)
*A61F 2/38* (2006.01)

(52) U.S. Cl.
CPC ............ *A61F 2/461* (2013.01); *A61F 2/3859* (2013.01); *A61F 2/4684* (2013.01); *A61F 2/4603* (2013.01);
(Continued)

(58) Field of Classification Search
CPC ....... A61B 17/88; A61B 17/92; A61F 2/4603; A61F 2/4605; A61F 2/4606;
(Continued)

(56) References Cited

U.S. PATENT DOCUMENTS 5,059,196 A * 10/1991 Coates .................... A61F 2/461
269/48.3
6,626,913 B1 9/2003 McKinnon et al.
(Continued)

FOREIGN PATENT DOCUMENTS

| CN | 104042303 A | 9/2014 |
| WO | 2004010882 A1 | 2/2004 |
| WO | 2017077324 A1 | 5/2017 |

OTHER PUBLICATIONS

Extended European Search Report for Application No. EP 18 19 1394.8 dated Jan. 24, 2019, 9 pages.
(Continued)

*Primary Examiner* — Samuel S Hanna
(74) *Attorney, Agent, or Firm* — Barnes & Thornburg LLP

(57) ABSTRACT

A surgical instrument system comprising a prosthetic trial component and an orthopaedic surgical instrument is disclosed. The orthopaedic surgical instrument includes a distal tip sized to be received in a passageway of the prosthetic trial component. When the distal tip is positioned in the passageway of the prosthetic trial component and is in an expanded position, the distal tip is configured to engage an inner surface of the prosthetic trial component to secure the prosthetic trial component to the orthopaedic surgical instrument and permit the extraction of the trial component from a patient's bone. A method of use is also disclosed.

6 Claims, 8 Drawing Sheets

(52) U.S. Cl.
CPC .............. *A61F 2002/4616* (2013.01); *A61F 2002/4627* (2013.01); *A61F 2002/4628* (2013.01)

(58) Field of Classification Search
CPC ...... A61F 2/4607; A61F 2/4609; A61F 2/461; A61F 2/4611; A61F 2/4612; A61F 2/4614; A61F 2002/4615; A61F 2002/4616; A61F 2/4618; A61F 2002/4619; A61F 2002/462; A61F 2002/4622
See application file for complete search history.

(56) References Cited

U.S. PATENT DOCUMENTS

| | | |
|---|---|---|
| 10,828,173 B2 | 11/2020 | Tsukayama et al. |
| 2004/0010262 A1 | 1/2004 | Parkinson et al. |
| 2007/0173856 A1 | 7/2007 | Parker |
| 2011/0213371 A1 | 9/2011 | Anthony et al. |
| 2013/0018382 A1 | 1/2013 | Jones et al. |
| 2016/0059403 A1 | 3/2016 | Mugnier |
| 2016/0100956 A1 | 4/2016 | Conley |
| 2016/0287236 A1 | 10/2016 | Garcia-Bengochea et al. |

OTHER PUBLICATIONS

English translation of Chinese Search Report for Application No. 201811074828.6, dated Oct. 2022, 3 pages.
English translation of Japanese Search Report for Application No. 2018-171294, dated Aug. 23, 2022, 5 pages.

\* cited by examiner

ORTHOPAEDIC SURGICAL INSTRUMENT SYSTEM AND METHOD FOR DETACHING TRIAL CONSTRUCT ASSEMBLIES

This divisional application claims priority under 35 U.S.C. § 121 to U.S. patent application Ser. No. 15/704,324, now U.S. Pat. No. 10,828,173, which is expressly incorporated herein by reference.

TECHNICAL FIELD

The present disclosure relates generally to orthopaedic surgical instrument systems, and, more particularly, to an orthopaedic surgical instrument for detaching or extracting a trial construct from a patient's bone.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Femoral components are designed to be attached to a surgically-prepared distal end of a patient's femur. Tibial trays are designed to be attached to a surgically-prepared proximal end of a patient's tibia.

To facilitate the replacement of the natural joint with the knee prosthesis, orthopaedic surgeons use a variety of orthopaedic surgical instruments such as, for example, prosthetic trial components, cutting blocks, drill guides, milling guides, and other surgical instruments. Prosthetic trial components, such as, for example, a femoral trial component and a tibial bearing trial component, are used to size and select the components of the knee prosthesis that will replace the patient's natural joint. A procedure that utilizes the trial components to size and select the components of the knee prosthesis is often referred to as a trial reduction.

SUMMARY

According to one aspect of the disclosure, an orthopaedic surgical instrument includes an elongated body extending along a longitudinal axis. The elongated body includes a distal tip configured to expand and contract relative to the longitudinal axis between an expanded position and a contracted position. A bore extends through the elongated body along the longitudinal axis. A rod is positioned within the bore and moveable along the longitudinal axis. The rod includes a distal end configured to selectively engage the distal tip of the elongated body to move the distal tip between the expanded position and the contracted position. A linkage assembly is coupled to a proximal end of the rod. The linkage assembly is moveable between a first position in which the distal end of the rod engages the distal tip of the elongated body and the distal tip is in the expanded position and a second position in which the distal end of the rod is disengaged from the distal tip and the distal tip is in the contracted position.

In some embodiments, the distal tip of the elongated body may have a tapered inner surface that defines a distal section of the bore. The distal end of the rod may be configured to engage the tapered inner surface when the linkage assembly is in the first position. In some embodiments, the inner surface may taper from a cylindrical inner surface to the tapered inner surface.

In some embodiments, the elongated body may have a central shaft and a plurality of cantilevered arms that extend outwardly from the central shaft. The plurality of cantilevered arms may define the distal tip of the elongated body. In some embodiments, the cantilevered arms may be positioned circumferentially around the bore. Each cantilevered arm may have a surface section of the tapered inner surface. In some embodiments, a slot may be defined between each cantilevered arm. Each slot may extend between the central shaft and an opening in the distal tip. In some embodiments, each cantilevered arm may have a distal flange extending radially outward from the longitudinal axis. In some embodiments, the distal flanges may define a first diameter when the distal tip is at the contracted position and a second diameter when the distal tip is at the expanded position. The second diameter may be greater than the first diameter.

In some embodiments, the linkage assembly may have a user-operated lever that extends outwardly from a slot in the elongated body. The lever may be rotatable about a pivot axis extending through the elongated body to move the linkage assembly between the first position and the second position. In some embodiments, the linkage assembly may have a link arm having a first end pivotally coupled to the rod and a second end pivotally coupled to the user-operated lever.

In some embodiments, a strike plate may extend outwardly from a proximal end of the elongated body.

According to another aspect of the disclosure surgical instrument system includes a femoral prosthetic trial component including a medial condyle spaced apart from a lateral condyle, an intercondylar notch positioned between the medial condyle and the lateral condyle, and a passageway that opens into the intercondylar notch. An orthopaedic surgical instrument includes an elongated body including a distal tip sized to be received in the passageway of the femoral prosthetic trial. A bore extends through the elongated body. A rod is positioned within the bore. The rod includes a distal end configured to selectively engage the distal tip of the elongated body to move the distal tip to an expanded position. When the distal tip is positioned in the passageway of the femoral prosthetic trial and is in the expanded position, the distal tip is configured to engage an inner surface of the femoral prosthetic trial to secure the femoral prosthetic trial to the orthopaedic surgical instrument.

In some embodiments, the femoral prosthetic trial component may have an annular groove that extends outwardly from the passageway. The annular groove may be partially defined by the inner surface. In some embodiments, a plurality of flanges may extend outwardly from the distal tip of the orthopaedic surgical instrument. Each flange may be sized to be received in the annular groove of the femoral prosthetic trial component. In some embodiments, the distal tip may be moveable to a contracted position. The flanges may define a first diameter when the distal tip is at the contracted position and a second diameter when the distal tip is at the expanded position. The second diameter may be greater than the first diameter.

In some embodiments, the rod may have a tapered outer surface that is configured to engage the distal tip of the elongated body to move the distal tip to the expanded position. In some embodiments, the distal tip of the elongated body may have a tapered inner surface that defines a distal section of the bore. A tapered outer surface of the rod may be configured to engage the tapered inner surface.

In some embodiments, the elongated body may have a central shaft and a plurality of cantilevered arms that extend outwardly from the central shaft. The plurality of cantilevered arms may define the distal tip of the elongated body.

According to another aspect of the disclosure, a method of detaching an orthopaedic prosthetic trial component from a patient's bone includes inserting a distal tip of an orthopaedic surgical instrument into an intercondylar notch of the orthopaedic prosthetic trial component. The method also includes advancing the distal tip distally into a passageway defined in the orthopaedic prosthetic trial component. The method also includes expanding the distal tip to engage a plurality of flanges of the orthopaedic surgical instrument with an inner surface of the orthopaedic prosthetic trial component. The method also includes moving the orthopaedic surgical instrument proximally to detach the orthopaedic prosthetic trial component from the patient's bone.

In some embodiments, expanding the distal tip to engage a plurality of flanges of the orthopaedic surgical instrument may require advancing the plurality of flanges into an annular groove positioned outward from the passageway.

BRIEF DESCRIPTION OF THE DRAWINGS

The detailed description particularly refers to the following figures, in which.

DETAILED DESCRIPTION OF THE DRAWINGS

Figure 1:
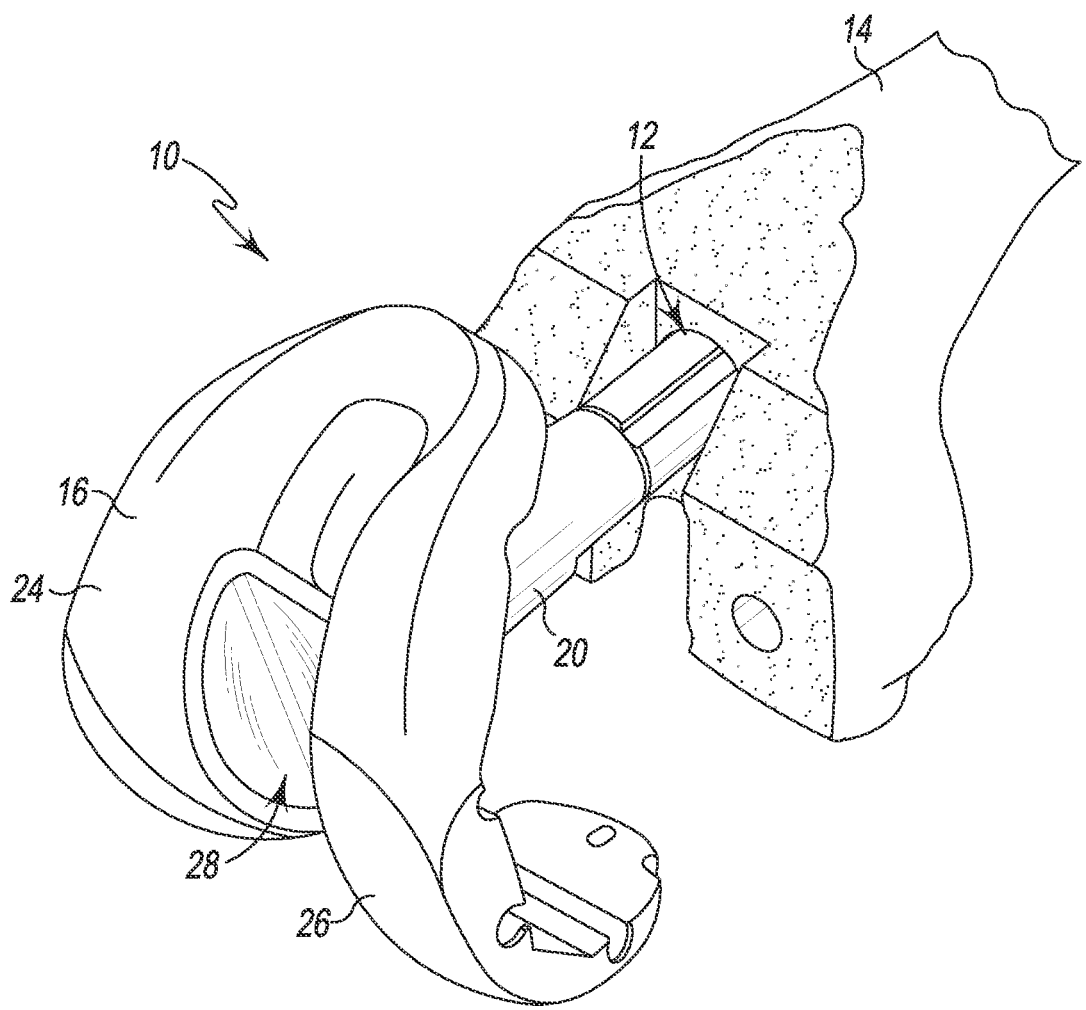
FIG. 1 is a perspective view of a femoral trial assembly being inserted into a cavity formed in a femur.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will also be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 2:
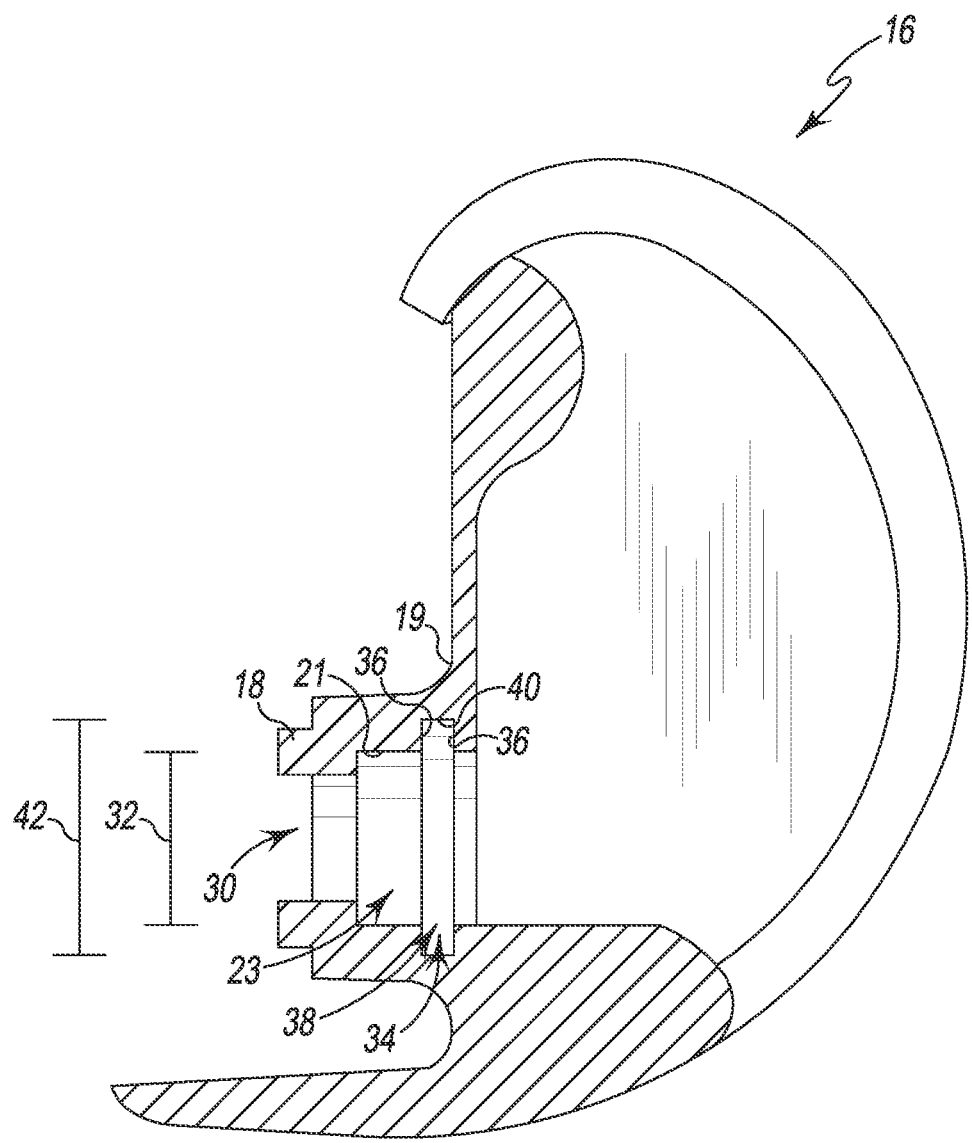
FIG. 2 is a cross-sectional elevation view of a surface trial component taken along line 2-2 in FIG. 1.

Referring now to FIGS. 1-2, a femoral trial construct assembly 10 for use in an orthopaedic surgical procedure is shown. In the illustrative embodiment, the femoral trial construct assembly 10 includes a femoral surface trial component 16 that is configured to be attached to a surgically-prepared surface of a patient's femur 14. The femoral trial construct assembly 10 also includes an elongated stem trial component 20 that is secured to the femoral surface trial component 16. The elongated stem trial component 20 is sized to be positioned in a surgically-prepared intramedullary canal 12 of the femur 14. During an orthopaedic surgical procedure, a surgeon may attach the femoral trial construct assembly 10 to the patient's femur 14 to evaluate the expected range of motion and size of a femoral prosthetic component assembly. The femoral trial construct assembly 10 may become fixed to the patient's femur 14 and, as a result, may be difficult to remove by hand. As described in greater detail below, the surgeon may utilize the surgical instrument 22, which is described in greater detail below, to extract or detach the femoral trial construct assembly 10 from the patient's femur 14. The embodiments described herein may also apply to any configuration of a femoral trial, whether it has a stem, off-set stem, or broach/sleeve trial attached.

As shown in FIG. 1, the femoral surface trial component 16 includes a medial condyle 24 that is spaced apart from a lateral condyle 26. The condyles 24, 26 are sized and shaped to articulate on corresponding bearing surfaces of a tibial trial component (not shown). An intercondylar notch 28 is defined between the condyles 24, 26 and is sized to receive a spine of the tibial trial component. In the illustrative embodiment, the configuration of the condyles 24, 26 and the intercondylar notch 28 mimics the configuration of a femoral prosthetic component. It should be appreciated that in other embodiments the femoral surface trial component may include one or more cutting slots such that the trial component can function as a cutting guide as well as a trial component.

As shown in FIG. 2, the femoral surface trial component 16 includes a housing 19 that connects the condyles 24, 26. A post 18 extends outwardly from the proximal surface of the housing 19. In the illustrative embodiment, the post 18 is sized and shaped to receive the distal end of the elongated stem trial component 20. A passageway 30 extends through the post 18 and opens into the intercondylar notch 28. The passageway 30 is sized to receive a fastener such as, for example, a threaded bolt (not shown), to secure the elongated stem trial component 20 to the post 18. It should be appreciated that in other embodiments the post may have a tapered outer surface, and the elongated stem component may have a tapered inner surface to permit the trial components 16, 20 to be joined together via a taper lock.

The femoral surface trial component 16 includes a cylindrical inner surface 21 that defines the distal section 23 of the passageway 30. In the illustrative embodiment, the inner surface 21 defines a diameter 32 of the distal section 23. As shown in FIG. 2, the femoral surface trial component 16 has an annular groove 34 that is defined in the inner surface 21. A pair of rim surfaces 36 extend inwardly from an opening 38 defined in the inner surface 21 to a cylindrical surface 40. In the illustrative embodiment, the surfaces 36, 40 cooperate to define the annular groove 34, which extends circumferentially around the passageway 30. In some embodiments, the rim surfaces 36 may be rounded, for example concave. In such an embodiment, the surfaces 36, 40 cooperate to define a partially torus-shaped annular groove 34. The cylindrical surface 40 has a diameter 42 that is greater than the diameter 32 of the passageway 30. As described in greater detail below, the surgical instrument 22 includes a distal tip 56 that is configured to be received in the annular groove 34 and is configured to engage a rim surface 36 to assist with the extraction of the femoral trial construct assembly 10 from the patient's femur 14.

Figure 3:
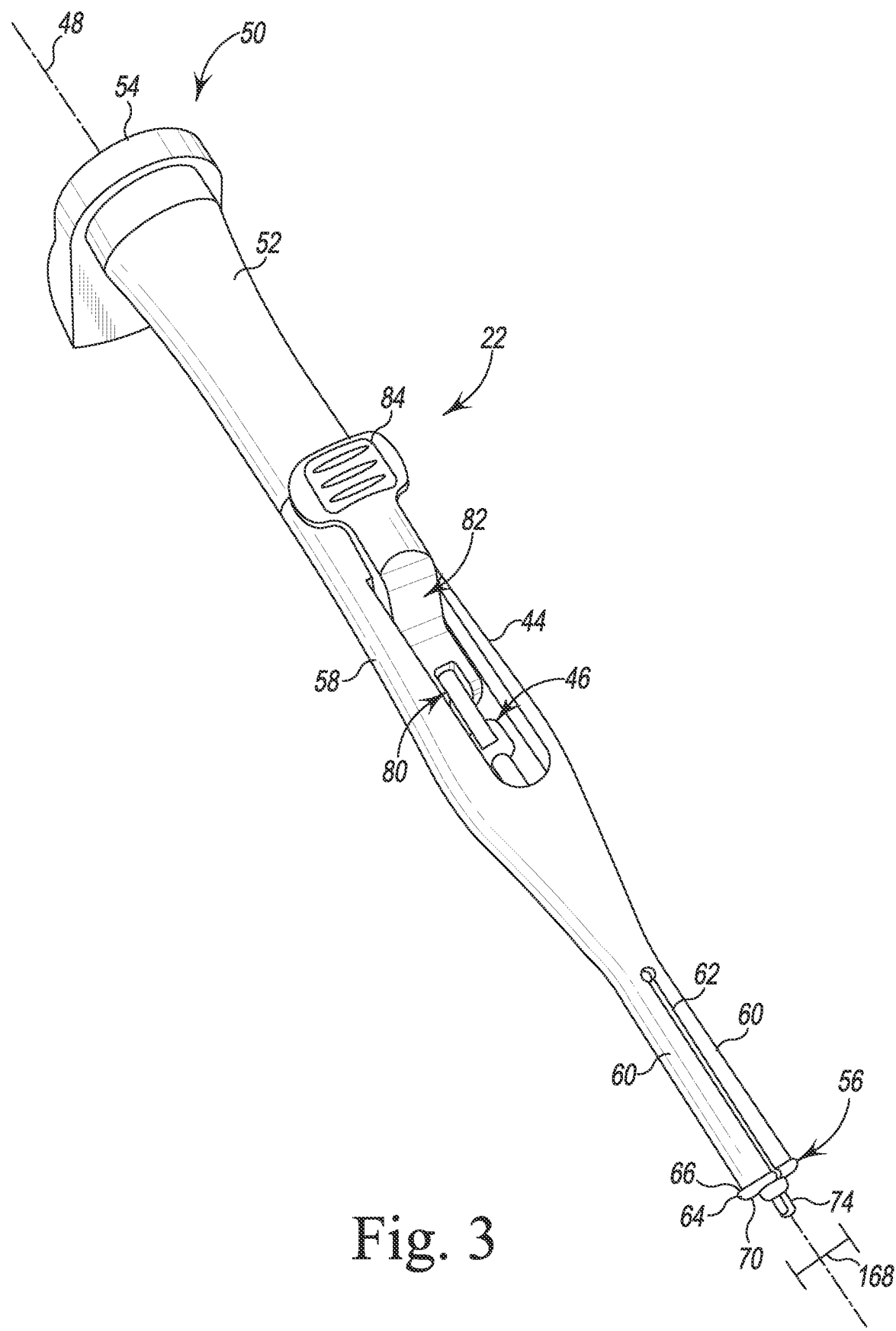
FIG. 3 is a perspective view of a surgical instrument for use in extracting the femoral trial assembly of FIG. 1 from a patient's bone.

Referring now to FIG. 3, the surgical instrument 22 includes an elongated body 44 that extends along a longitudinal axis 48 between a proximal end 50 and the distal tip 56. The surgical instrument 22 includes a strike plate 54 that extends outwardly from the proximal end 50 of the elongated body 44. The strike plate 54 includes a wedge directly opposed from a lever 84 (described in more detail below). The configuration of the strike plate 54 encourages the user to orient the strike plate 54 as needed for ease of extraction and allows the user to hold the lever 84 (if needed) to stabilize the instrument 22 during extraction. A distal surface of the strike-plate 54 is flat, while a proximal surface has a non-uniform profile to discourage impaction. The strike plate 54 also has a central hole with a threadform that allows for attachment of a slaphammer for assistance during extraction of a femoral trial with a broach. The elongated body 44 has a grip 52 that is positioned adjacent to the strike plate 54, which may be grasped by a surgeon or other user to manipulate the surgical instrument 22 and position the distal tip 56 within the passageway 30 of the femoral surface trial component 16. As described in greater detail below, the surgical instrument 22 also includes an actuation mechanism 46 that is operable to expand the distal tip 56 to advance the distal tip 56 into the annular groove 34 of the femoral surface trial component 16.

The elongated body 44 includes a central shaft 58 and a plurality of cantilevered arms 60 that extend outwardly from an end of the central shaft 58. The cantilevered arms 60 extend along the longitudinal axis 48 to the distal tip 56. The central shaft 58 and the cantilevered arms 60 are formed from a metallic metal such as, for example, stainless steel. In the illustrative embodiment, the shaft 58 and arms 60 are formed as a single monolithic component. It should be appreciated that in other embodiments the shaft 58 and the arms 60 may be formed as separate components that are later assembled to form the elongated body 44.

Each cantilevered arm 60 has a distal flange 64 positioned at the distal tip 56 of the elongated body 44. Each distal flange 64 extends radially outwardly from the longitudinal axis 48, and the flanges 64 cooperate to define a diameter 168 when the distal tip 56 is not expanded. Each distal flange 64 includes a proximal engagement surface 66 and a distal tapered surface 70 that is positioned opposite the engagement surface 66. As described in greater detail below, the engagement surfaces 66 of the flanges 64 are configured to engage a rim surface 36 of the femoral surface trial component 16 when the distal tip 56 is expanded.

In the illustrative embodiment, the elongated body 44 includes three cantilevered arms 60 that are arranged around the longitudinal axis 48. The cantilevered arms 60 are separated by three slots 62 that are defined between each adjacent pair of cantilevered arms 60. It should be appreciated that in other embodiments the elongated body 44 may include additional cantilevered arms or may include only two cantilevered arms. When the distal tip 56 is not expanded, the cantilevered arms 60 extend parallel to the longitudinal axis 48.

As described above, the surgical instrument 22 also includes an actuation mechanism 46 that is operable to expand the distal tip 56. In the illustrative embodiment, the actuation mechanism 46 includes an elongated rod 74 that is configured to move along the axis 48 relative to the cantilevered arms 60 and a linkage assembly 82 that is operable to move the elongated rod 74. The linkage assembly 82 is positioned in an oblong slot 80 defined in the elongated body 44. A lever 84 of the linkage assembly 82 extends outwardly from the oblong slot 80 to a position above the elongated body 44. The lever 84 is configured to be operated by a user to change the position of the rod 74 relative to the cantilevered arms 60 and thereby cause the distal tip 56 to expand.

Figure 4:
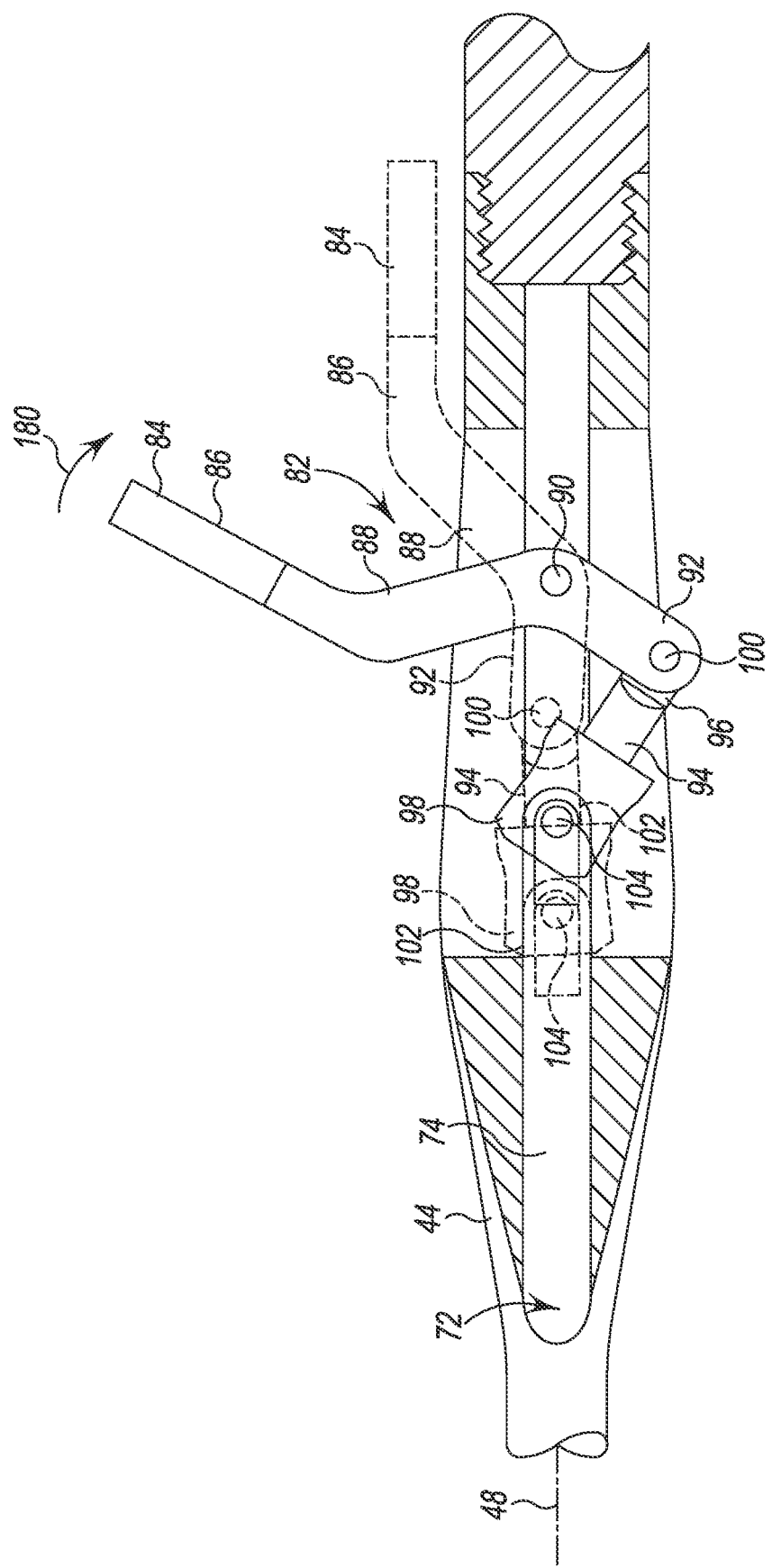
FIG. 4 is a cross-sectional elevation view of a portion of the surgical instrument taken along line 4-4 shown in FIG. 3.

Referring now to FIG. 4, the linkage assembly 82 includes the lever 84 and a link 94 that extends between the lever 84 and the elongated rod 74. In the illustrative embodiment, the lever 84 includes a main body 88 that is pivotally coupled to the elongated body 44 via a pin 90. An outer lever arm 86 extends outwardly from the main body 88 and out of the oblong slot 80 to define a user-operated button. The lever 84 also includes a drive lever arm 92 that extends outwardly from the main body 88 opposite from the outer lever arm 86. In the illustrative embodiment, the lever 84 is formed from a metallic material such as, for example, stainless steel, and is formed as a single monolithic component. It should be appreciated that in other embodiments the lever 84 may be formed as separate components that are later assembled.

The tip of the drive lever arm 92 is coupled to an end 96 of the link 94 via a pin 100. The opposite end 98 of the link 94 is coupled to the proximal end 102 of the rod 74 via a pin 104. Each of the pins 90, 100, 104 define pivot axes about which the linkage assembly 82 pivots during use to cause the rod 74 to move relative to the cantilevered arms 60, as described in greater detail below. The link 94 and pins 90, 100, 104 are formed from a metallic material such as, for example, stainless steel.

Figure 5:
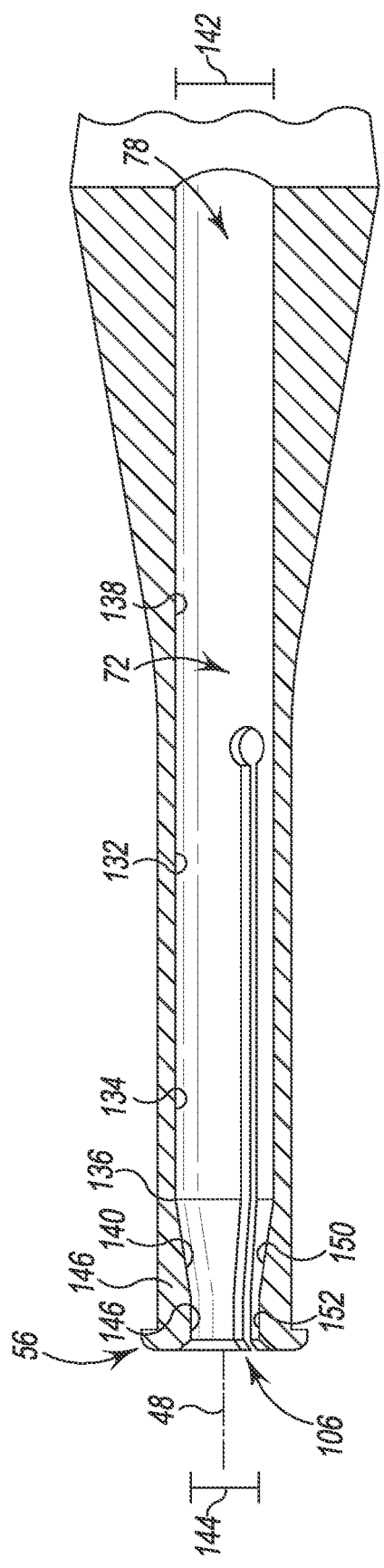
FIG. 5 is a cross-sectional view of a distal tip of the surgical instrument taken along line 5-5 shown in FIG. 3.

In the illustrative embodiment, the elongated rod 74 is positioned in a bore 72 defined in the elongated body 44 along the longitudinal axis 48. Referring now to FIG. 5, the bore 72 is defined by an inner surface 132 that extends from a proximal opening 78 that is connected to the oblong slot 80. The inner surface 132 extends to a distal opening 106 defined in the distal tip 56 of the surgical instrument 22. The inner surface 132 includes a cylindrical section 138 that extends from the proximal opening 78 and has a diameter 142. Each cantilevered arm 60 includes a curved surface 134 that defines part of the cylindrical section 138 of the inner surface 132. Each curved surface 134 extends to an edge 136 of the cylindrical section 138 positioned near the distal tip 56.

The inner surface 132 includes a tapered section 140 that extends along the longitudinal axis 48 from the edge 136 to another edge 146 that is connected to a smaller cylindrical section 148. Each cantilevered arm 60 includes a curved tapered surface 150 that defines part of the tapered section 140 and a curved surface 152 that defines part of the cylindrical section 148. The cylindrical section 148 extends to the distal opening 106 of the elongated body 44. As shown in FIG. 5, the cylindrical section 148 has a diameter 144 when the distal tip 56 is not expanded. The diameter 144 is smaller than the diameter 142 of the cylindrical section 138.

Figure 6:
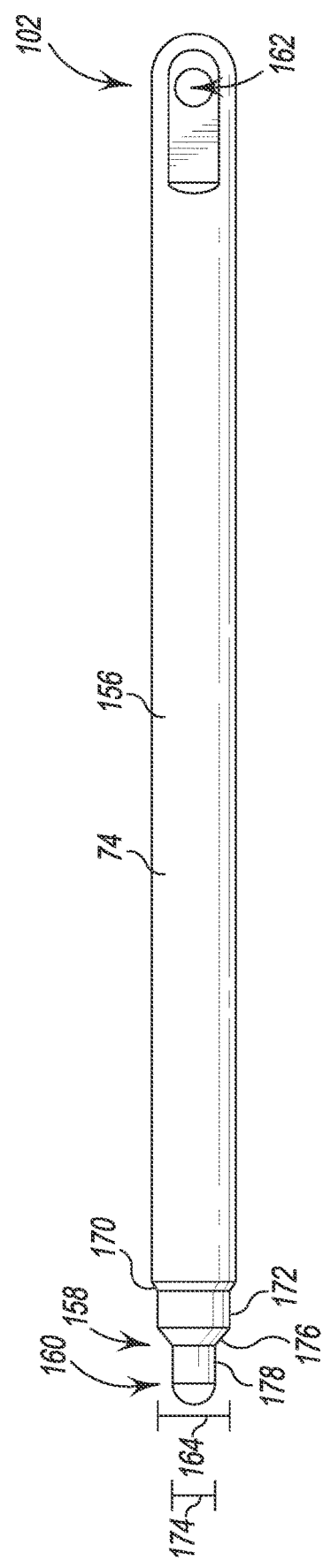
FIG. 6 is a plan view of a rod of the surgical instrument shown in FIG. 3.
Figure 7:
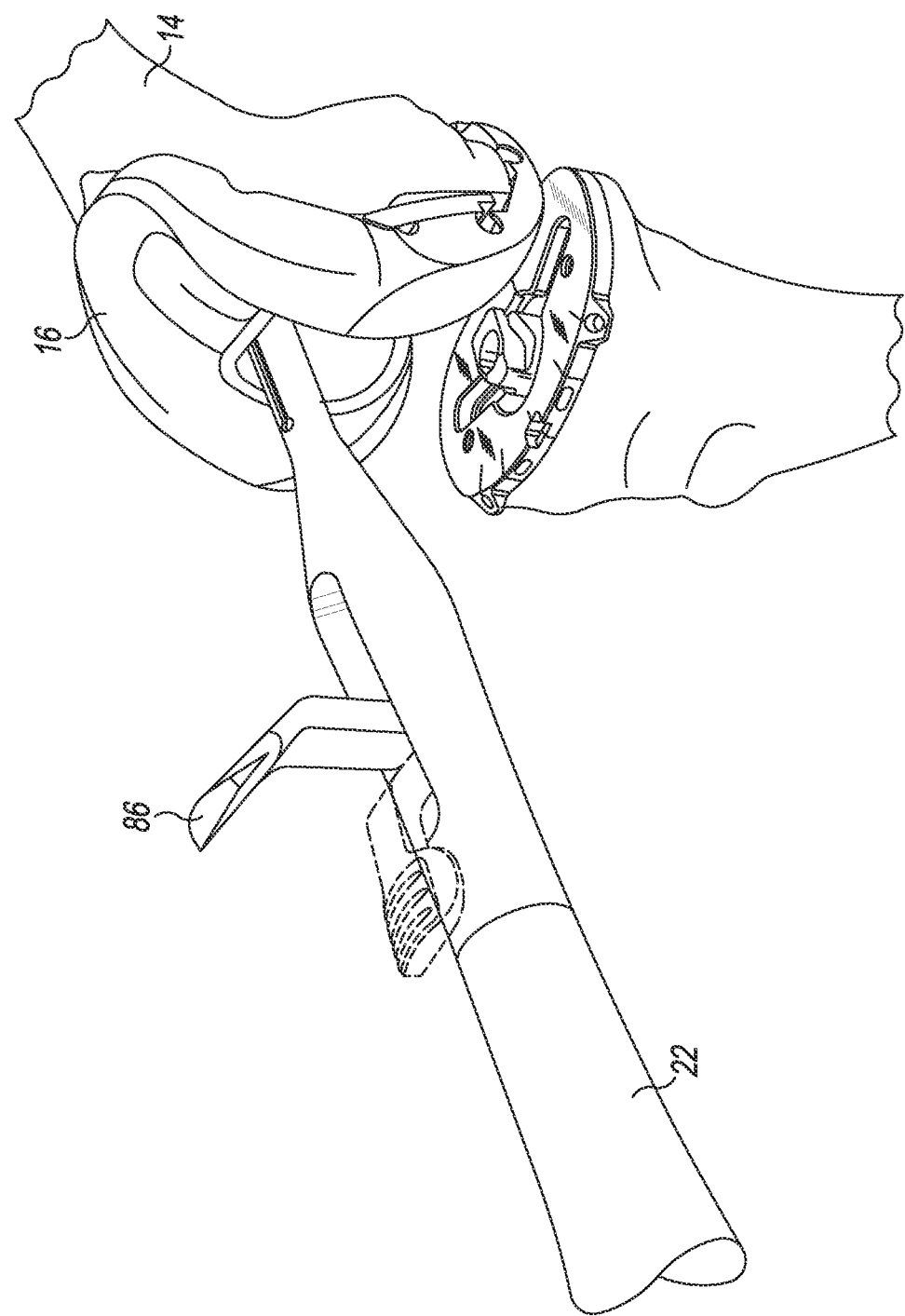
FIG. 7 is a perspective view of the surgical instrument shown in FIG. 3 being advanced into a passageway of the femoral surface trial shown in FIG. 2.

Referring now to FIG. 6, the elongated rod 74 includes a shaft 156 that extends from the proximal end 102 to a distal end 160. A through hole 162 is defined in the proximal end 102 and is sized to receive the pin 104 to connect the elongated rod 74 to the link 94 of the linkage assembly 82. In the illustrative embodiment, the shaft 156 includes a cylindrical outer surface that has a diameter 164 that is substantially equal to the diameter 142 of the bore 72 defined in the elongated body 44. The elongated rod 74 is formed from a metallic material such as, for example, stainless steel, and is formed as a single monolithic component in the illustrative embodiment.

The distal end 160 of the elongated rod 74 includes a ram head 158 configured to engage the curved tapered surfaces 150 of the cantilevered arms 60 to expand the distal tip 56 of the surgical instrument 22. In the illustrative embodiment, the ram head 158 includes a tapered surface 170 that extends from the shaft 156 to a cylindrical pin 172. The cylindrical pin 172 has an intermediate diameter 174 that is less than the diameter 164 of the shaft 156. In the illustrative embodiment, the diameter 174 is substantially equal to the diameter 144 of the elongated body 44 (i.e., the diameter of the opening 106 when the distal tip 56 is not expanded). The cylindrical pin 172 extends to another tapered surface 176 of the ram head 158, which extends inwardly to a peg 178. As shown in FIG. 6, the peg 178 has a rounded tip that defines the distal-most surface of the elongated rod 74.

In use, the linkage assembly 82 may be actuated to advance the elongated rod 74 along the bore 72 and engage the ram head 158 with the curved tapered surfaces 150 of the cantilevered arms 60. To do so, the surgeon or other user may operate the outer lever arm 86 of the lever 84 to move the linkage assembly 82 from the unlocked position shown in solid line in FIG. 4 to the located position shown in broken line in FIG. 4 and in solid line in FIG. 3. When the user applies a force in the direction indicated by the arrow 180 in FIG. 4, the lever 84 is pivoted about the pin 90 to move the outer lever arm 86 toward the elongated body 44.

The rotation of the lever 84 about the pin 90 causes the drive lever arm 92 to pivot upward toward the longitudinal axis 48 of the elongated body 44, thereby moving the pin 100 distally along the axis 48. As the pin 100 moves distally, the link 94 rotates about the pin 100 and the pin 104 and moves to a position substantially parallel with the longitudinal axis 48. The movement of the link 94 applies force to the proximal end 102 of the elongated rod 74 in the direction indicated by arrow 182, thereby urging the rod 74 to move distally.

The distal movement of the rod 74 advances the tapered surface 176 of the ram head 158 into engagement with the curved tapered surfaces 150 of the cantilevered arms 60, thereby applying a radially outward force on the cantilevered arms 60. The continued movement of the rod 74 distally advances the cylindrical pin 172 of the ram head 158 into engagement with the curved tapered surfaces 150 of the cantilevered arms 60 and then advances the tapered surface 170 of the ram head 158 into contact with the curved tapered surfaces 150 of the cantilevered arms 60 and increasing diameter defined by the distal tip 56.

When the linkage assembly 82 is in the locked position, the pins 100, 104 are positioned on the longitudinal axis 48 and the drive lever arm 92 and the link 94 extend along the longitudinal axis 48. The cylindrical outer surface of the shaft 156 of the elongated rod 74 is positioned in contact with the curved surfaces 152 of the cantilevered arms 60 (which define the smaller cylindrical section 148 of the bore 72). The peg 178 of the elongated rod 74 extends outwardly from the distal opening 106 of the elongated body 44, and the distal tip 56 of the surgical instrument 22 is in the expanded position. In the expanded position, the distal flanges 64 define an expanded diameter 190 (see FIG. 9), which is greater than the diameter 32 defined in the femoral surface trial component 16.

Figure 8:
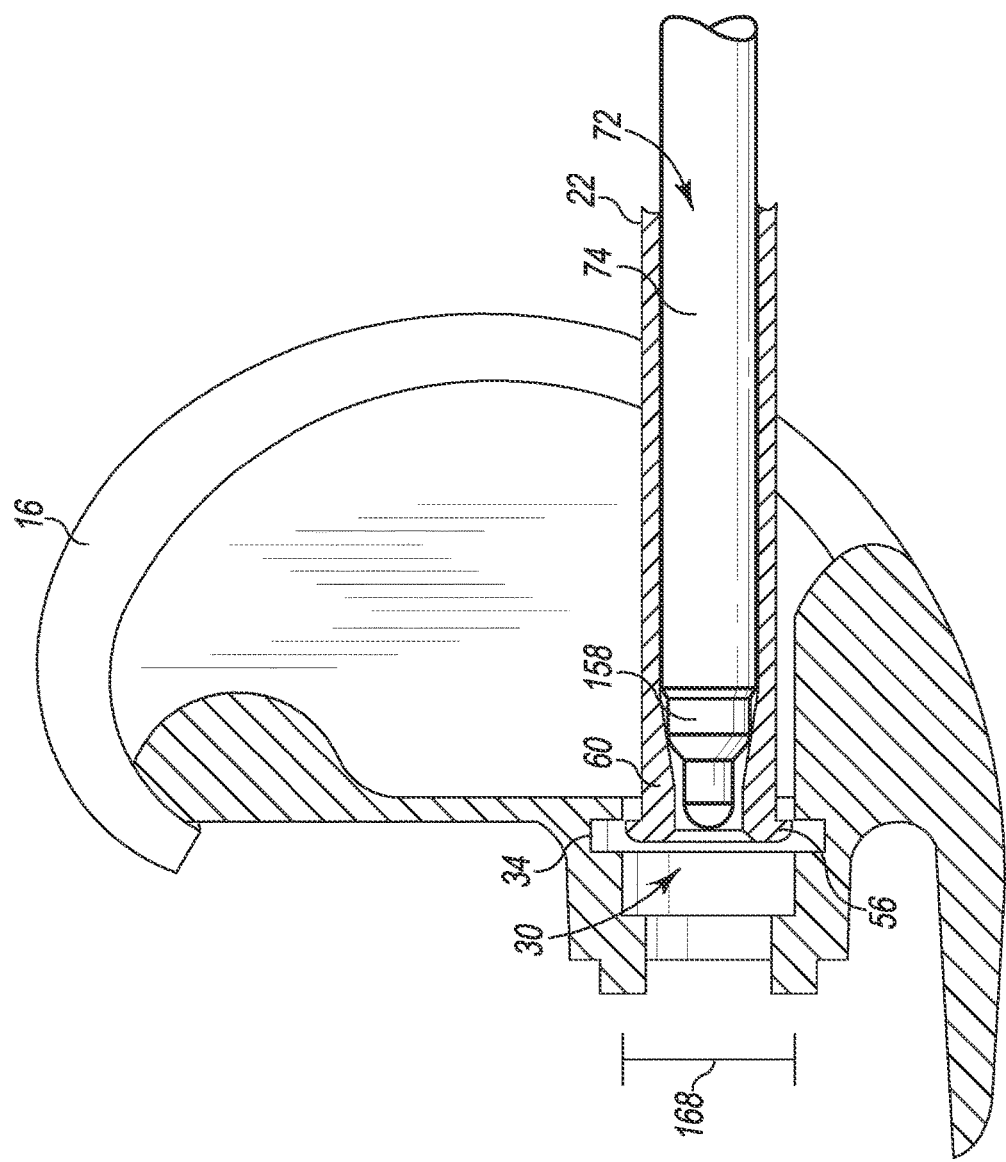
FIG. 8 is a cross-sectional view showing the surface trial component and the distal tip of the surgical instrument positioned in the surface trial component.

To remove a femoral surface trial component 16 fixed to a patient's femur 14, the surgeon may operate the outer lever arm 86 to move the linkage assembly 82 (and hence the rod 74) to the unlocked position such that the distal tip 56 of the instrument 22 has the diameter 168. As shown in FIG. 8, the surgeon may then advance the distal tip 56 into the passageway 30 defined in the femoral surface trial component 16. When the distal tip 56 is aligned with the annular groove 34 of the femoral surface trial component 16, the surgeon may actuate the outer lever arm 86 to move the linkage assembly 82 to the locked position. As described above, as the linkage assembly 82 moves from the unlocked position to the locked position, the elongated rod 74 slides distally along the bore 72 to engage the ram head 158 with the cantilevered arms 60 to apply a radially outward force that expands the distal tip 56 from the diameter 168 to the diameter 190.

Figure 9:
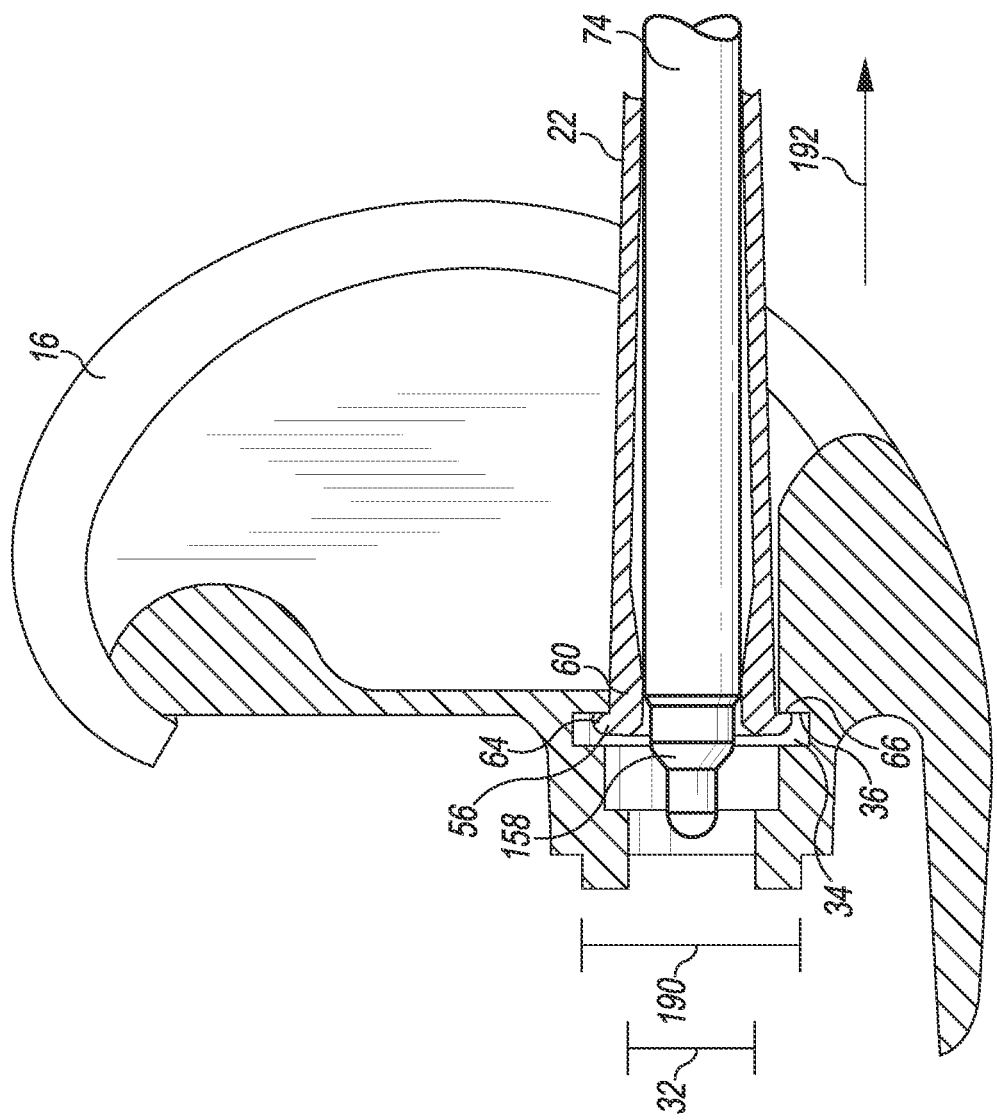
FIG. 9 is a cross-sectional view similar to FIG. 8 showing the distal tip of the surgical instrument positioned therein in an expanded position.

As the distal tip 56 is expanded, the distal flanges 64 of the surgical instrument 22 advance into the annular groove 34 of the femoral surface trial component 16, as shown in FIG. 9. With the distal tip 56 expanded, the engagement surfaces 66 of the distal flanges 64 engage the distal rim surface 36 of the annular groove 34. With the ram head 158 extended, the ram head 158 positions within an opening defined in a stem bolt (not shown) positioned within the passageway 30 of the femoral surface trial component 16. The ram head 158 is positioned within the stem bolt to prevent displacement of the surgical instrument 22 relative to the longitudinal axis 48. In some cases, there may not be sufficient material for the annular groove 34 to be a complete full-circle and only a partial groove is achievable and the groove breaks through the wall of the femoral trial. In such cases, the ram head 158 engages the bolt head for stability since it is possible for one of the cantilever arms 60 to not engage with any part of the annular groove 34 due to the annular groove 34 breaking through the wall of the femoral trial. Accordingly, the cantilevered arms 60 can still expand with one arm 60 floating with respect to the groove 34 and fully contained within the body of the femoral trial. The surgeon may then apply a force (via the strike plate 54 or by pulling on the grip 52) in the direction indicated by arrow 192 to detach the femoral surface trial component 16 (and any stem trial component 20) from the patient's femur 14. When applying force, the elongated body 44 of the surgical instrument 22 defines a load path for extraction of the femoral surface trial component 16. The surgeon may then continue with the orthopaedic surgical procedure. At the conclusion of the procedure, the surgical instrument 22 may be autoclaved or otherwise sterilized and made ready for use in another surgical procedure.

It should be appreciated that, although the surgical instrument 22 is described with respect to extracting the femoral surface trial component 16, the surgical instrument 22 may also be modified to enable impaction of the femoral surface trial component 16. For example, the distal tapered surface 70 of the distal flange 64 may be formed as a flat surface that is configured to engage the proximal rim surface 36 of the annular groove 34. In such a configuration, the elongated body 44 of the surgical instrument 22 may provide a load path for impacting the femoral surface trial component 16. Impaction may be achieved by applying a force via the strike plate 54 or by pushing on the grip 52. While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. For example, although the orthopaedic surgical instrument has been shown and described in reference to extracting or detaching a femoral surface trial component, it should be appreciated that in other embodiments the orthopaedic surgical instrument may be used to extract a tibial surface trial component and its associated stem trial component. In other embodiments, the orthopaedic surgical instrument may be used to extract or detach trial components from other joints of a patient's bone such as, for example, the hip, shoulder, or ankle joints. In other embodiments, orthopaedic surgical instrument may be used to extract or detach other surgical instruments such as cutting blocks from a patient's bone.

There are a plurality of advantages of the present disclosure arising from the various features of the devices and assemblies described herein. It will be noted that alternative embodiments of the devices and assemblies of the present disclosure may not include all of the features described yet still benefit from at least some of the advantages of such features. Those of ordinary skill in the art may readily devise their own implementations of the devices and assemblies that incorporate one or more of the features of the present invention and fall within the spirit and scope of the present disclosure as defined by the appended claims.

The invention claimed is:

1. A method of detaching a femoral prosthetic trial component from a patient's femur, the method comprising:
   inserting a distal tip of an orthopaedic surgical instrument into an intercondylar notch of the femoral prosthetic trial component,
   advancing the distal tip proximally through the intercondylar notch and into a passageway defined in a post of the femoral prosthetic trial component, the post extending proximally away from a proximal bone facing surface of the femoral prosthetic trial component and positioned in an intramedullary canal of the patient's femur,
   moving a rod of the orthopedic surgical instrument into engagement with the distal tip so as to expand the distal tip such that a plurality of flanges of the orthopaedic surgical instrument are received into an annular groove formed in an inner surface of the post of the femoral prosthetic trial component so as to secure the orthopaedic surgical instrument to the femoral prosthetic trial component, and
   moving the orthopaedic surgical instrument distally to detach the femoral prosthetic trial component from the patient's femur.

2. The method of claim 1, wherein moving the rod into engagement with the distal tip includes advancing the plurality of flanges into the annular groove positioned circumferentially around the passageway.

3. The method of claim 1, wherein:
   the orthopaedic surgical instrument comprises a lever, and
   moving the rod into engagement with the distal tip comprises moving the lever from an unlocked position to a locked position.

4. The method of claim 3, wherein the lever is positioned in the unlocked position during insertion of the distal tip of the orthopaedic surgical instrument into the intercondylar notch of the femoral prosthetic trial component.

5. The method of claim 3, wherein the lever is positioned in the locked position during movement of the orthopaedic surgical instrument proximally to detach the femoral prosthetic trial component from the patient's femur.

6. The method of claim 1, wherein:
   the orthopaedic surgical instrument comprises a lever, and
   moving the rod into engagement with the distal tip comprises moving the lever from an unlocked position to a locked position.

\* \* \* \* \*